United States Patent [19]

Ramachandran et al.

[11] Patent Number: 4,987,239

[45] Date of Patent: Jan. 22, 1991

[54] PROCESS FOR THE PRODUCTION OF ANHYDRIDES

[75] Inventors: Ramakrishnan Ramachandran, Allendale; Yagya Shukla, Roselle Park; Donald L. MacLean, Annandale, all of N.J.

[73] Assignee: The BOC Group, Inc., Murray Hill, N.J.

[21] Appl. No.: 356,971

[22] Filed: May 24, 1989

Related U.S. Application Data

[63] Continuation-in-part of Ser. No. 216,037, Jul. 7, 1988, Pat. No. 4,868,330, which is a continuation-in-part of Ser. No. 178,117, Apr. 6, 1988, abandoned, which is a continuation-in-part of Ser. No. 124,731, Nov. 24, 1987, abandoned.

[51] Int. Cl.$^5$ ................... C07D 307/33; C07D 307/89
[52] U.S. Cl. .................................... 549/250; 549/248; 549/249; 549/262
[58] Field of Search ................ 549/262, 248, 249, 250

[56] References Cited

U.S. PATENT DOCUMENTS 3,904,652 9/1975 Frank .
4,352,755 10/1982 Higgens et al. ..................... 549/258

FOREIGN PATENT DOCUMENTS 2544972 4/1977 Fed. Rep. of Germany .
3521272 12/1986 Fed. Rep. of Germany .
88/04199 6/1980 PCT Int'l Appl. .

OTHER PUBLICATIONS

M. Malow, "Benzene or Butane for MAN," *Hydrocarbon Processing*, pp. 149–153 (Nov. 1980).
H. Bosch et al., "Selective Oxidation of n-Butane to Maleic Anhydride Under Oxygen-Deficient Conditions Over V-P-O Mixed Oxides," *Applied Catalysis*, 323–337 (1987).
D. L. Trimm, *Design of Industrial Catalysts*, pp. 176–187, Elsevier Scientific Publishing Company (1980).
S. C. Arnold et al., "Use Fluid Bed Reactor for Maleic Anhydride from Butane," *Hydrocarbon Processing*, pp. 123–126 (Sep. 1985).

*Primary Examiner*—Joseph Paul Brust
*Attorney, Agent, or Firm*—Carol A. Nemetz; Robert I. Pearlman

[57] ABSTRACT

An improved process is provided for the production of anhydrides from hydrocarbons by reaction with an oxygen-containing gas comprising oxygen, air or a gas enriched in oxygen relative to air, in the presence of a suitable catalyst. In the process, a selective separator provides recycle of a substantial portion of the unreacted hydrocarbon as well as for a controlled amount of a gaseous flame suppressor in the system. The gaseous flame suppressor comprises a substantially unreactive hydrocarbon containing 1 to 5 carbon atoms, carbon dioxide, and nitrogen when present in the feed to the oxidation reactor. The use of air or oxygen-enriched air in the feed to the oxidation reactor is particularly advantageous from an economic view in combination with a pressure swing adsorption unit as the selective separator. The process is characterized by high selectively to the formation of the anhydride product.

20 Claims, 4 Drawing Sheets

PROCESS FOR THE PRODUCTION OF ANHYDRIDES

RELATED APPLICATIONS

This application is a continuation-in-part of U.S. patent application Ser. No. 07/216,037, filed July 7, 1988, now U.S. Pat. No. 4,868,330, which, in turn, is a continuation-in-part of U.S. patent application Ser. No. 07/178,117, filed Apr. 6, 1988, now abandoned, which, in turn, is a continuation-in-part of U.S. patent application Ser. No. 07/124,731, filed Nov. 24, 1987 and now abandoned.

FIELD OF THE INVENTION

The present invention is directed to a process for producing anhydrides from hydrocarbons and an oxygen-containing gas in the presence of a suitable catalyst under conditions which achieve increased efficiency and selectivity toward the desired product.

BACKGROUND OF THE PRIOR ART

The production of anhydrides by oxidation of an appropriate hydrocarbon in the presence of a suitable catalyst is well known. The production of maleic anhydride, for example, from a gaseous feed of butane and air is described by M. Malow, "Benzene or Butane for MAN," 59 *Hydrocarbon Processing* 149–153, (November 1980).

Typically, maleic anhydride is produced by vapor phase oxidation of normal butane (n-butane) over a vanadium-phosphorus oxide catalyst. The reaction produces carbon monoxide, carbon dioxide, water, and smaller amounts of other partially oxidized byproducts in addition to maleic anhydride. The reaction can be carried out either in a fixed, fluidized, or transport bed reactor.

Federal Republic of Germany (FRG) patent application Disclosure No. 25 44 972 ('972) discloses that after maleic anhydride recovery, 75 to 98% of the off-gas is recycled. From the remaining gas, butane is recovered using a two-bed TSA (temperature swing adsorption) process. The TSA is a very energy intensive method to recover butane. Also, this process removes only about 1.5 to 18.4% of the nitrogen in the air feed to the maleic anhydride reactor but not all the CO and $CO_2$ produced in the maleic anhydride reactor This will result in considerable inert gas accumulation and a reduction in reaction efficiency. Hence, this process requires operation either at a high pressure or with the use of almost pure oxygen to maintain maleic anhydride production as compared to a once-through process.

A process to recover unreacted hydrocarbon by condensation is shown by U.S. Pat. No. 4,352,755. Butane recovery by condensation is an energy intensive method, especially since, after recovery, butane has to be reheated to the reaction temperature. Also, if the feed contains nitrogen, the cooling duty required for condensation will be tremendous.

More recently, Federal Republic of Germany patent application Disclosure No. 35 21 272 ('272) shows a process using pure oxygen and butane as feed to a fixed bed reactor, with the feed concentration of oxygen below the stoichiometric ratio. The '272 patent suggests that the oxidation reactor is operated at a very low butane conversion. The unreacted butane is recovered and recycled from the off-gases following maleic anhydride recovery by compressing and flashing it to remove butane, $CO_x$, maleic anhydride, and water. It is estimated that the pressure required to achieve the above is very high. Again, this butane recovery scheme is energy intensive and may not be practical when the feed contains nitrogen.

H. Bosch et al., "Selective Oxidation of n-Butane to Maleic Anhydride under Oxygen-Deficient Conditions over V-P-O Mixed Oxides," 31 *Applied Catalysis* 323–337, at 335 (1987) concludes that operation of the process in oxygen-deficient conditions would result in lower than normal maleic anhydride yields. Since typical oxidation catalysts must always be kept in oxidized form, a lower butane conversion coupled with limited oxygen in the process could result in catalyst deactivation.

U.S. Pat. No. 3,904,652 shows a process where, after maleic anhydride recovery from the reactor effluent gases, off-gases containing unreacted butane, nitrogen, $CO_x$, and oxygen is recycled to the reactor. About 11% of the off-gas is purged to avoid inert gas (e.g., $CO_2$, $N_2$) build up in the process. However, about 7% of fresh butane fed to the reactor is lost in the purge, and the necessary incineration of this purge requires additional fuel.

It is therefore apparent that industry is still searching for a cost effective process of converting hydrocarbons into anhydrides. The process of the present invention is cost effective and the disadvantages of the aforementioned systems are substantially reduced or eliminated therein. Moreover, in comparison to conventional processes, the thermal energy requirements of the present invention are markedly reduced.

SUMMARY OF THE INVENTION

A process is disclosed for the production of anhydrides comprising reacting in a suitable reactor a hydrocarbon and an oxygen-containing gas, preferably oxygen-enriched air, in the presence of an oxidation catalyst under operating conditions which produce the desired product at relatively low feed hydrocarbon conversion and relatively high product selectivity. The product stream is quenched or scrubbed with a liquid to form a liquid phase containing the desired product and a gas phase which is introduced into a suitable selective separator, preferably a pressure swing adsorption unit, to separate substantially all of the unreacted hydrocarbon which is recycled to the reactor. The process provides an effective amount of a gaseous flame suppressor, if required, i.e. from about 30 to about 95 percent by volume, in the gas stream which is introduced into the selective separator.

DETAILED DESCRIPTION OF THE INVENTION

In the process of this invention, a hydrocarbon is reacted with an oxygen-containing gas comprising pure oxygen, air or a gas enriched in oxygen relative to air in the presence of an oxidation catalyst. Suitable oxidation catalysts are those that will catalyze the production of the desired anhydride under the conditions utilized in the reactor. These catalysts and their use are conventional and well known to one of ordinary skill in the art. The term "hydrocarbon" as utilized herein includes both aliphatic and aromatic compounds. Preferably the hydrocarbon starting materials are olefins or xylenes, although formation of an anhydride directly from an alkane by appropriate choice of catalyst is clearly within the scope of the present invention. Maleic anhydrides are produced from alkanes and alkenes, and phthalic anhydrides are produced from xylenes and naphthalenes with the former being preferred.

Illustrative of products, and their respective starting materials, which can be advantageously produced by the method of this invention are phthalic anhydride from o-xylene, maleic anhydride from n-butane, maleic anhydride from n-butylene, and the like. While the subject process will be described with reference to the production of maleic anhydride from n-butane, the present invention is not intended to be limited thereto.

Figure 1:
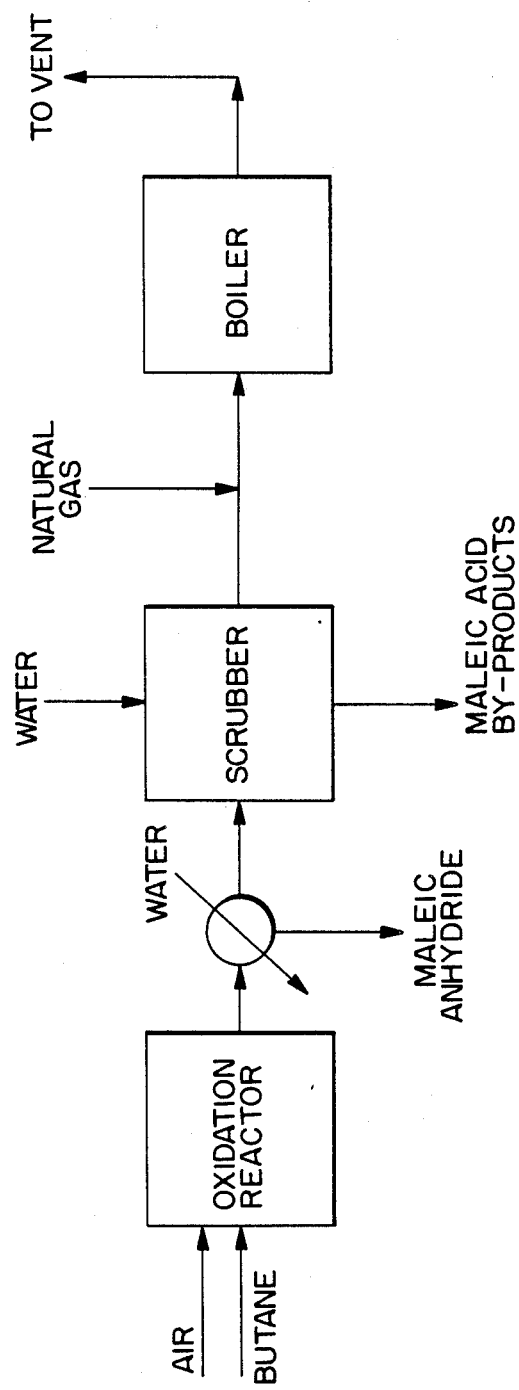
FIG. 1 illustrates in a block diagram a conventional process of producing maleic anhydride.

A known process to produce maleic anhydride is illustrated in FIG. 1. Butane and air are fed into a conventional reactor containing a suitable oxidation catalyst. The reactor may be of any conventional fixed, fluidized, or transport bed design. Such processes, which do not involve a recycle step, can utilize air or oxygen-enriched air in the reactor feed, although air is normally used for reasons of economy. The oxygen concentration in the reactor feed is not considered critical with regard to the accumulation of other gases, primarily nitrogen, in the system due to the lack of recycle, though the oxygen content must be regulated with respect to other factors, e.g., to maintain catalyst performance.

The reactor product gases are cooled in a series of heat exchangers, not shown, to form steam. The cooled gases are passed to a specially designed separator where partially condensed maleic anhydride is recovered, and then uncondensed vapors are passed to a water or solvent column or tower for scrubbing to dissolve the products, i.e. maleic anhydride, acetic acid, furan, crotonaldehyde and other byproducts. The maleic anhydride is subsequently recovered from the scrubbed solution by conventional methods. The off-gases from the scrubber are combined with natural gas and combusted in a boiler to generate steam. The off-gases of the boiler are vented. Since there is no recycle provided in such a process, the yield of maleic anhydride realized is directly related to the efficiency of the reactor.

Figure 2:
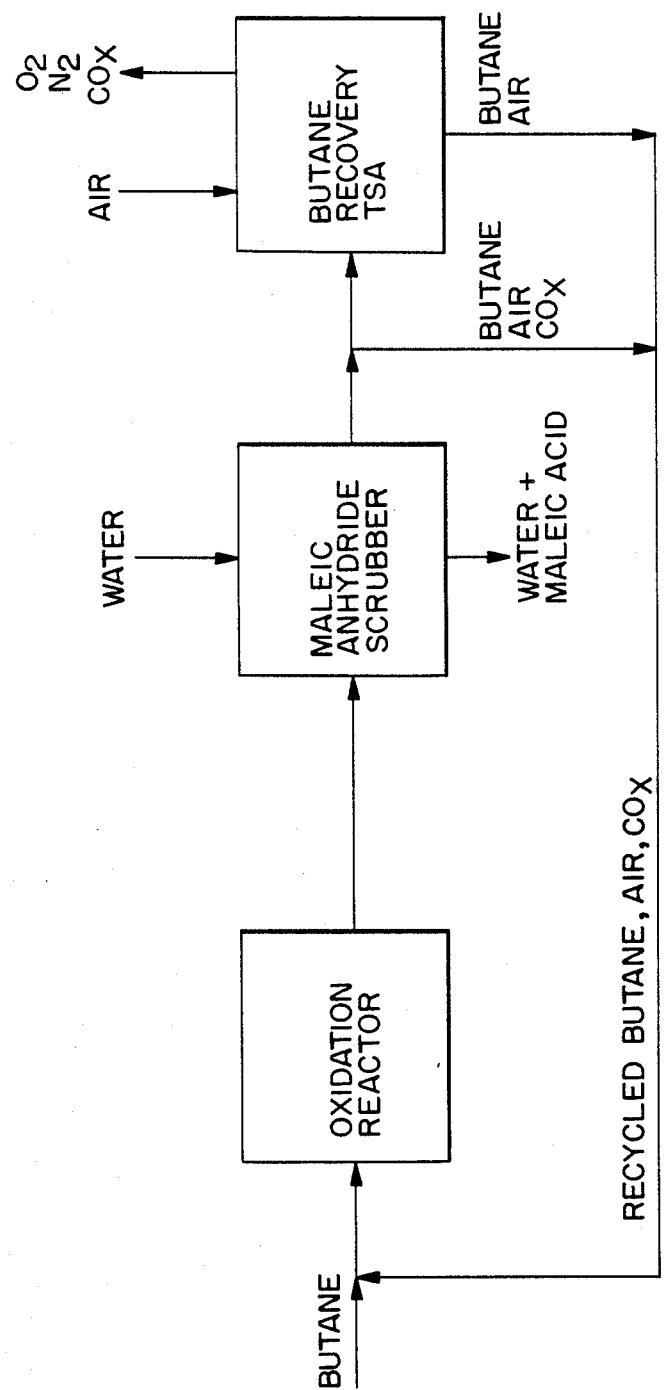
FIG. 2 illustrates in a block diagram another conventional process, producing maleic anhydride utilizing a recycle step.

FIG. 2 illustrates a cyclic process for the production of maleic anhydride, e.g., FRG patent application Disclosure No. 25 44 972 ('972). In this process, butane along with recycled butane, air and $CO_x$ are fed into a fixed bed oxidation reactor containing suitable catalyst to produce maleic anhydride. The reactor off-gases are cooled and scrubbed using water to recover the product as maleic acid. Maleic acid can then be dehydrated to produce maleic anhydride by conventional methods. The scrubber off-gases are divided into two portions, a majority (75 to 98%) of which is returned directly to the oxidation reactor while the remaining portion is further processed in a thermal swing adsorption (TSA) system to recover butane. Fresh air, fed into the TSA beds at 140° C. for regeneration, and recovered butane is recycled to the oxidation reactor. When only a small portion of the scrubber off-gases is withdrawn for separation, $CO_x$ and nitrogen accumulate in the system, resulting in excessive reactor pressures. This limitation restricts the oxidant feed to the maleic anhydride reactor of the '972 to essentially pure oxygen.

TSA processes are generally slow and very energy intensive. Applicants estimate that the substantial heat duty of the '972 TSA process will be about 9300 kilocalorie for every standard liter per hour of butane recovered. If a large purge is withdrawn from the scrubber off-gases, and air is utilized as the oxidant, the total heat requirement for the TSA may render the overall process uneconomical. Also, the '972 patent teaches that fresh air is fed into the TSA beds at 140° C. to regenerate them; since the beds are filled with butane, substantial flammability dangers are presented.

In contrast to the prior art processes illustrated in FIGS. 1 and 2, the process of the present invention provides a selective separator, preferably a pressure swing adsorption (PSA) unit, which effectively removes a substantial portion of the reactant hydrocarbon so that it can be recycled to the oxidation reactor, thus providing high maleic anhydride yield and economy of operation. As utilized herein, the expression "a substantial portion," as it pertains to recycle of the reactant hydrocarbon, means at least about 80 percent by volume where the oxygen-containing gas in the feed to the oxidation reactor is air; means at least about 90 percent by volume where a mixture of equal parts of pure oxygen and air is utilized as the oxygen-containing gas; and means at least about 95 percent by volume where the oxygen-containing gas is pure oxygen. In each instance, these are minimum percents. Utilizing pure oxygen as the oxygen-containing gas, for example, the amount of reactant hydrocarbon recycled is typically 97 to 99 percent by volume.

As the selective separator contemplated herein typically requires a pressurized feed, the process of the present invention provides an effective amount of a gaseous flame suppressor to minimize the flammability potential at the point or points in the cycle where the pressure is increased. Although it is preferred to locate the means to raise the pressure, e.g. a compressor, in the gaseous effluent from the scrubber, it may be located at other appropriate locations in the cycle. The gaseous flame suppressor of the present invention comprises a substantially unreactive hydrocarbon having from 1 to 5 carbon atoms, carbon dioxide and, where air or enriched air is utilized as the oxygen-containing gas in the feed to the oxidation reactor, nitrogen. By "substantially unreactive" is meant that at least 90 percent by volume of the hydrocarbon component of the gaseous flame suppressor will pass through the oxidation reactor unchanged. The substantially unreactive hydrocarbon can be a saturated or unsaturated hydrocarbon with saturated being preferred.

The amount of the gaseous flame suppressor mixture in the subject cyclic process is controlled so that it will be maximized at the point or points in the system where it is of greatest advantage, i.e. the feed to the pressure raising means. By "maximize," it is meant that the amount of flame suppressor is optimum to achieve a minimum flammability potential with a margin of safety within the constraints of the systems, i.e. without sacrifice of the primary object of efficiently producing the desired anhydride. The amount of the gaseous flame suppressor is such that, regardless of the location of the means to increase pressure, the gaseous effluent from the scrubber will contain from about 30 to about 95 percent by volume thereof. It will be appreciated that, when pure oxygen is utilized as the oxygen-containing gas in the feed to the oxidation reactor, nitrogen will not be a component in the gaseous flame suppressor. In embodiments of the subject process to be described herein, each of the components of the gaseous flame suppressor mixture of the present invention will comprise a major portion thereof.

Examples of specific substantially unreactive hydrocarbons utilized as a component of the subject gaseous flame suppressor and the reaction in which they are utilized include: methane for the production of maleic anhydride from n-butane; n-butane for the production of maleic anhydride from n-butylene; methane for the production of phthalic anhydride from xylene; and the like.

Unreacted hydrocarbon reactant, e.g. n-butane, while not a major portion of the gaseous flame suppressor, appears to enhance the flame suppressant capacity thereof. The amount of unreacted reactant hydrocarbon present in the gaseous flame suppressor mixture will depend on the percent per-pass conversion of the reactant hydrocarbon entering the oxidation reactor which is converted to products. Those skilled in the art will appreciate that factors such as choice of catalyst, operating temperatures, space velocity and the like, can be adjusted to have the oxidation reactor operate at a desired conversion of the reactant hydrocarbon in the feed thereto. At lower operating conversions, e.g. 60 percent conversion, there will be a greater amount of unreacted reactant hydrocarbon circulating in the system. For example, using substantially pure oxygen in an oxidation reactor operating at 80 percent conversion in accordance with the invention, there will be only about 2 to 10 percent unreacted reactant hydrocarbon in the scrubber effluent whereas, at 60 or 90 percent conversion, there will be a greater or lesser, respectively, of unreacted reactant hydrocarbon in the scrubber effluent. The composition of the gaseous flame suppressor will be adjusted accordingly.

The process of this invention is advantageous in that it provides the efficiency of recycle afforded by the process illustrated in FIG. 2, yet is free of the disadvantages inherent therein while, at the same time, being less complex. The advantages of the present invention are, in large measure, provided by the incorporation into the process of a selective separator which retains a substantial portion of the unreacted reactant hydrocarbon in the system. The gaseous flame suppressor of the subject process may be partially or totally recycled, depending on the operating conditions and feed to the system. In a preferred embodiment, the separator is a pressure swing adsorption unit. However, the present invention comprises absorption and cryogenic methods of separation.

The efficiency of the selective separator of the present invention permits operation of the system at low conversion, i.e. a reduction from the conventional object of achieving the highest possible once through yield of feed material to products. Reducing conversion will, in turn, increase selectivity with a given catalyst to the desired product. A substantial economic benefit is realized on an industrial scale even from a one percent increase in selectivity to the desired product, which is achieved by the present process since it retains and recycles a very high percentage of unreacted reactant hydrocarbon. Reducing conversion from present levels of about 95% to about 80% will produce a one percent increase in selectivity. Therefore, in the context of the present invention, "low conversion" is that level of conversion below the maximum possible, such that at least about one percent increase in selectivity is achieved with a given catalyst. Low conversion as utilized herein, therefore, can be 80 percent or even higher if the desired increase in selectivity is produced.

Conversion per pass, selectivity and yield utilized in the above discussion are defined as follows:

$$\text{Conversion Per Pass} = \frac{H_R}{H_F} \times 100$$

$$\text{Selectivity} = \frac{P_P}{H_R} \times 100$$

$$\text{Yield} = \frac{P_P}{H_F} \times 100$$

where
$H_R$ = moles of reactive hydrocarbon reacted
$H_F$ = moles of reactive hydrocarbon fed
$P_P$ = moles of desired product produced Pressure swing adsorption (PSA) is a well known process for seParating the components of a mixture of gases by virtue of the difference in the degree of adsorption among them on a particulate adsorbent retained in a stationary bed. Typically, two or more such beds are operated in a cyclic process comprising adsorption under relatively high pressure and desorption or bed regeneration under relatively low pressure or vacuum. The desired component or components may be obtained during either of these stages. The cycle may contain other steps in addition to the fundamental steps of adsorption and regeneration, and it is commonplace to have two or more adsorbent beds cycled 180° out of phase to assure a pseudo continuous flow of desired product. While it is conventional for the adsorption step of a PSA cycle to be carried out under pressure, it can run at ambient pressure with desorption under vacuum. It is the difference in pressure between the adsorption and desorption stages which is essential for operation of the system.

Figure 3:
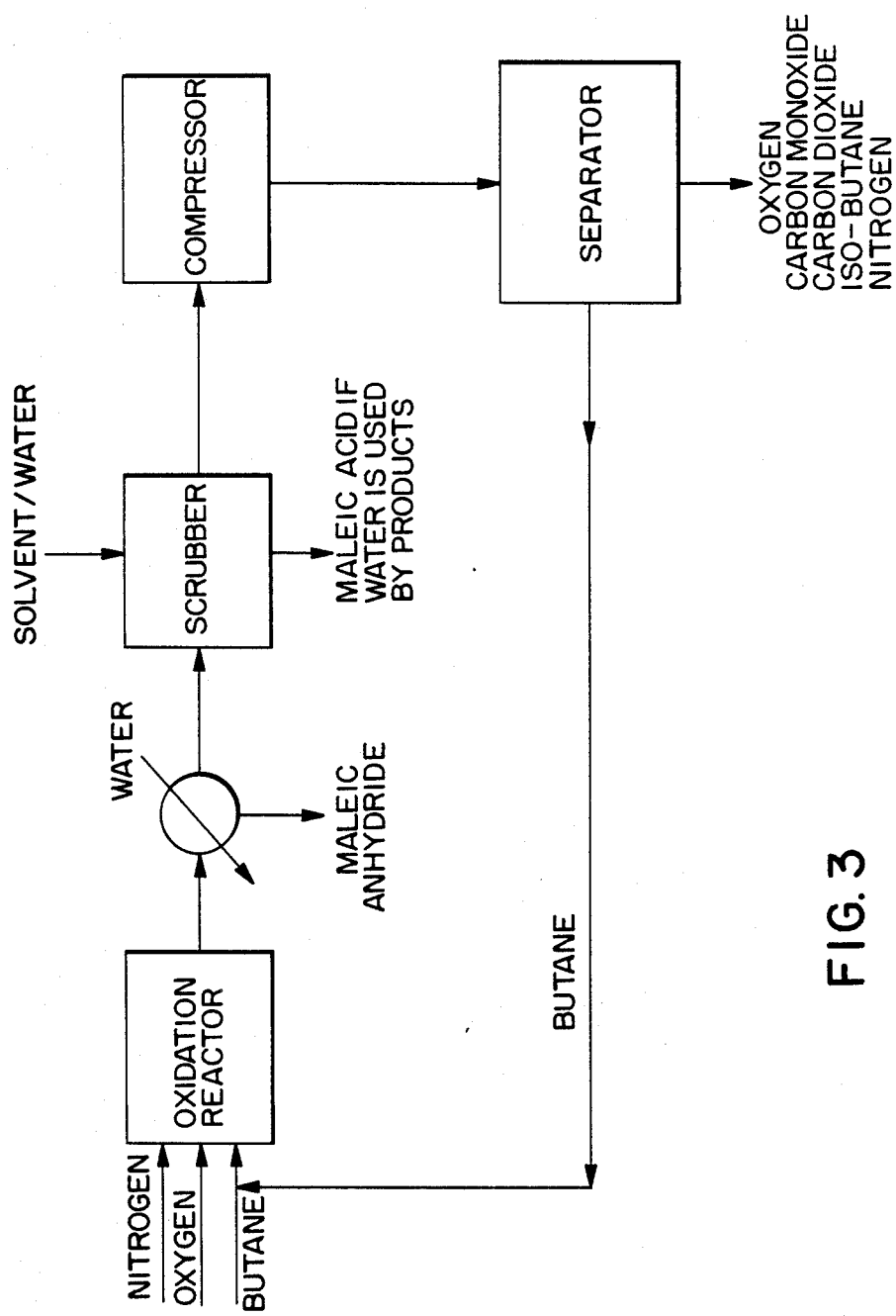
FIG. 3 illustrates in a block diagram an embodiment of a process for producing maleic anhydride in accordance with the present invention utilizing air or oxygen-enriched air as a feed to the oxidation reactor, and a pressure swing adsorption unit as the separator, wherein the gaseous flame suppressor contains a substantial amount of nitrogen.

FIG. 3 shows a process for producing maleic anhydride where the feed into a conventional oxidation reactor comprises n-butane and air or oxygen-enriched air. In accordance with this invention, oxygen-enriched air preferably contains from about 30 to about 80, most preferably from about 55 to 65, percent by volume of oxygen. Such mixtures may be produced by adjusting the capacity of a conventional oxygen-producing unit, e.g. a conventional PSA unit, or by mixing pure oxygen with air in the proper proportions. The use of oxygen-enriched air will produce a minimum concentration of nitrogen in the feed to the oxidation reactor of from about 10 to 30 percent by volume of the feed into the reactor depending on the operating conversion of the reactor as discussed above. The minimum concentration of nitrogen in the reactor feed will result in the desired level of nitrogen in the feed to the compressor for the PSA unit separator as discussed hereafter.

The oxidation reactor utilized in the present process is conventional and may employ either a fixed, fluidized, or transport catalyst bed. A typical oxidation reactor is shown in S. C. Arnold et al., "Use Fluid Bed Reactor for Maleic Anhydride from Butane," 64 *Hydrocarbon Processing* 123–126, at 124 (September 1985), and in the PCT Pub. No. WO88/04199 (June 16, 1988). The reactor contains a conventional oxidation catalyst, supported or unsupported, such as vanadium-phosphorus oxide, vanadium-molybdenum oxide, cobalt-molybdenum oxide, manganese-molybdenum oxide and the like. Other suitable catalysts are disclosed, for example, in D. L. Trimm, *Design of Industrial Catalysts* at 179–187, Elsevier Scientific Publishing Company (1980). Additional suitable catalysts are known to those skilled in the art.

The oxidation reaction is conducted at a temperature of from about 250° to 600° C., preferably from about 300° to 500° C., and at low pressures, typically in the range of from about 2 to 50 psig, preferably from about 3 to 30 psig. The reactants are passed through the reactor at a velocity in the range of from about 0.5 to 5.0 ft/sec. The ratio of oxygen to n-butane in the feed is suitably in the range of 0.3:1 to 10:1 by volume.

The oxidation reaction results in the production of a major amount of maleic anhydride and minor amounts of acetic acid, furan, crotonaldehyde, methyl vinyl ketone, and carbon oxides as well as unreacted oxygen, n-butane and, where air or oxygen-enriched air is used in the feed, nitrogen. In the present embodiment, methane, the flame suppressor, is substantially recycled from the PSA unit. The reactor product gases are cooled in a series of heat exchangers to form steam, and cooled gases are passed through a specially designed separator where partially condensed maleic anhydride is recovered. The uncondensed vapors are scrubbed with a liquid to dissolve the soluble compounds for subsequent separation and recovery of maleic anhydride.

The gas phase effluent from the scrubber is introduced into a PSA unit separator wherein unreacted n-butane is separated from the other gases in the mixture. Although the adsorption stage of the PSA unit can be at ambient pressure, it is preferred to introduce the scrubber gaseous effluent into the PSA unit as a pressurized feed. Experience has shown that the flammability potential in the system is greatest in the compressor or other means utilized to increase the pressure. Therefore, the total amount of gaseous flame suppressor is maximized at the feed into the compressor, preferably disposed in the scrubber gaseous effluent to minimize the flammability potential. The operating conditions of the system are adjusted to provide for this.

The gas phase effluent from the scrubbing tower preferably contains, on a volume basis, from about 3 to 16 percent of carbon monoxide, from about 0.5 to 12 percent of n-butane, from about 0.5 to 10 percent of oxygen, from about 10 to 40 percent of carbon dioxide, from about 30 to 80 percent of nitrogen, and from about 3 to 20 percent of methane, the latter three comprising the gaseous flame suppressor. It must be borne in mind that this example is given relative to the synthesis of maleic anhydride from n-butane utilizing oxygen-enriched air containing approximately 60 percent by volume of oxygen as the oxygen-containing feed to the oxidation reactor which is operating at 60 percent conversion of the n-butane. More preferably, the volume percent of butane, nitrogen and carbon monoxide in the scrubber effluent is from about 20 to 95 percent by volume. In the process illustrated in FIG. 3, the preferred selective separator is a PSA unit operating under pressure provided by a compressor. The compressor increases the pressure of the scrubber gaseous phase to the preferred operating pressure of a PSA unit, typically in the range of from about 3 to 50 psig, preferably from about 10 to 30 psig. The range of preferred operating pressure may vary to an extent depending on the adsorbent utilized.

The adsorbent in the PSA unit may be any art-recognized material which adsorbs n-butane to a substantially greater degree than methane or carbon dioxide. Silica gel and molecular sieve zeolite (e.g. 4A), alone or in combination, are preferred adsorbent materials.

By proper selection of the adsorbent in the PSA unit, the operation thereof can readily be controlled utilizing art-recognized manipulations so that the recycle stream formed therein contains a substantial portion of the n-butane and lesser percentages of methane and carbon dioxide. The nitrogen, oxygen and the remainder of the carbon oxides and methane are withdrawn from the system, preferably combusted, and vented. It is contemplated herein to recover oxygen from the vent stream and recycle it to the reactor feed to enhance the operation of the system.

Utilizing a system, as shown in FIG. 3, for the production of maleic anhydride utilizing oxygen-enriched air containing approximately 60 percent by volume of oxygen as a reactor feed and a mixture of nitrogen, carbon dioxide and methane as the gaseous flame suppressor, with nitrogen comprising a major portion thereof, the flow rates in mole percent at critical points in the system were determined and are presented in Table I. The feed was obtained by mixing equal parts of air and pure oxygen. The compositions are expressed in mole percent and based on 100 moles of maleic anhydride produced, and a total flow is stated in moles. The data expressed in Table I represents operation of the system under conditions such that 60 percent and 80 percent, respectively, of the n-butane feed to the oxidation reactor is converted to products for each feed. In Table I, Point A is the feed into the oxidation reactor, Point B is effluent therefrom, Point C is the feed to the compressor, Point D is the recycle stream from the PSA separator, and Point E is the vent stream from the PSA separator.

TABLE I

| Component | A | B | C | D | E |
|---|---|---|---|---|---|
| 60 Percent Conversion - Equal parts pure oxygen and air | | | | | |
| Methane | 7.8 | 7.1 | 10.6 | 18.7 | 1.1 |
| n-Butane | 11.9 | 4.4 | 6.5 | 11.5 | 0.7 |
| Oxygen | 32.6 | 3.0 | 4.5 | 1.7 | 7.7 |
| CO | 1.4 | 6.5 | 9.7 | 3.6 | 16.9 |
| $CO_2$ | 20.2 | 22.2 | 33.1 | 51.3 | 11.8 |
| Maleic Anhydride | — | 4.3 | — | — | — |
| Water | — | 28.4 | — | — | — |
| Nitrogen | 26.1 | 24.0 | 35.7 | 13.3 | 61.8 |
| Total Flow, moles | 2125.4 | 2313.3 | 1555.7 | 837.1 | 718.7 |
| 80 Percent Conversion - Equal parts pure oxygen and air | | | | | |
| Methane | 7.4 | 6.8 | 9.9 | 17.6 | 1.1 |
| n-Butane | 8.7 | 1.6 | 2.3 | 4.1 | 0.2 |
| Oxygen | 32.6 | 3.0 | 4.4 | 1.6 | 7.6 |
| CO | 1.5 | 7.0 | 10.2 | 3.8 | 17.6 |
| $CO_2$ | 23.8 | 26.1 | 38.3 | 59.8 | 13.6 |
| Maleic Anhydride | — | 3.9 | — | — | — |
| Water | — | 27.8 | — | — | — |
| Nitrogen | 26.0 | 23.8 | 34.9 | 13.1 | 60.0 |
| Total Flow, moles | 2367.3 | 2585.3 | 1765.7 | 943.9 | 821.8 |

TABLE I-continued

| Component | A | B | C | D | E |
|---|---|---|---|---|---|
| 60 Percent Conversion - Air | | | | | |
| Methane | 3.2 | 3.1 | 3.6 | 10.8 | 0.3 |
| n-Butane | 4.8 | 1.9 | 2.2 | 6.6 | 0.2 |
| Oxygen | 15.1 | 3.0 | 3.5 | 2.2 | 4.1 |
| CO | 0.6 | 2.8 | 3.3 | 2.1 | 3.8 |
| $CO_2$ | 8.2 | 9.5 | 11.1 | 29.5 | 2.7 |
| Maleic Anhydride | — | 1.9 | — | — | — |
| Water | — | 12.2 | — | — | — |
| Nitrogen | 68.1 | 65.7 | 76.4 | 48.8 | 89.0 |
| Total Flow, moles | 5207.4 | 5395.3 | 4637.8 | 1453.4 | 3184.3 |
| 80 Percent Conversion - Air | | | | | |
| Methane | 3.0 | 2.9 | 3.4 | 10.2 | 0.2 |
| n-Butane | 3.5 | 0.7 | 0.8 | 2.4 | 0.1 |
| Oxygen | 15.1 | 3.0 | 3.5 | 2.2 | 4.0 |
| CO | 0.6 | 3.0 | 3.5 | 2.2 | 4.0 |
| $CO_2$ | 9.7 | 11.2 | 13.0 | 34.6 | 3.1 |
| Maleic Anhydride | — | 1.7 | — | — | — |
| Water | — | 12.0 | — | — | — |
| Nitrogen | 68.0 | 65.5 | 75.9 | 48.4 | 88.5 |
| Total Flow, moles | 5792.3 | 6010.3 | 5190.6 | 1628.6 | 3562.0 |

Figure 4:
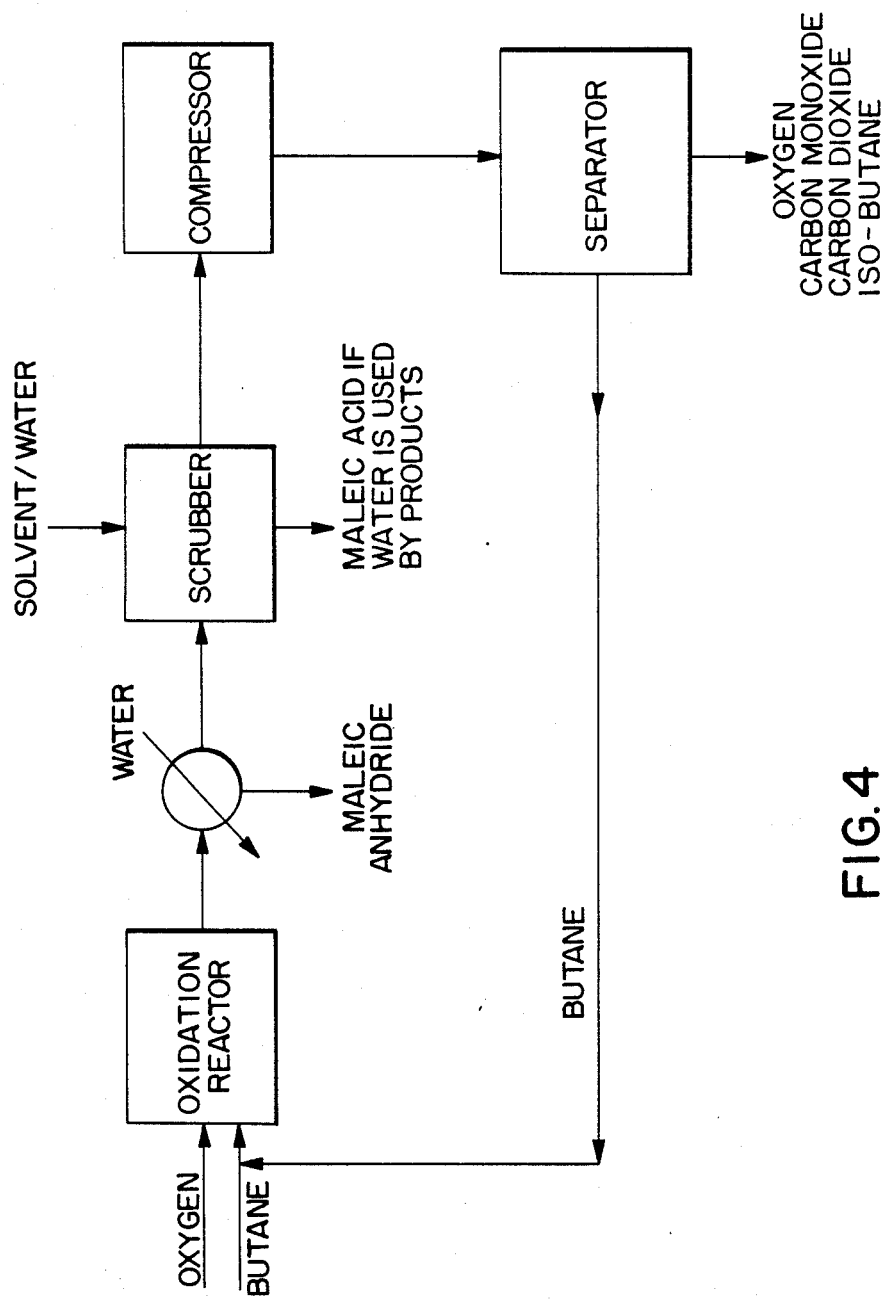
FIG. 4 illustrates in a block diagram an embodiment of a process of producing maleic anhydride in accordance with this invention wherein the gaseous flame suppressor contains a substantial amount of a saturated hydrocarbon such as methane.

In FIG. 4, there is illustrated a system utilizing a pure oxygen feed to the reactor wherein the gaseous flame suppressor is comprised of methane and carbon dioxide. In the system shown in FIG. 4, the gas phase effluent from the scrubber is introduced into a separator, preferably a PSA unit, to separate the n-butane and methane for recycle to the combined reactor feed. As in the system shown in FIG. 3, the volume percent of methane in the reactor feed is determined so as to produce a concentration in the gaseous feed from the scrubber to the compressor which, in combination with the carbon dioxide present, will minimize flammability potential.

The gas phase effluent from the scrubbing tower preferably contains, on a volume basis, from about 0.5 to 12 percent of n-butane, from about 0.5 to 10 percent of oxygen, from about 10 to 65 percent of carbon dioxide, from about 3 to 16 percent of carbon monoxide and from about 5 to 50, preferably about 10 to 40 percent, of methane. More preferably, the combined volume percent of n-butane, methane and carbon dioxide in the scrubber effluent is from about 30 to 95 percent by volume.

Utilizing a system as shown in FIG. 4 for the production of maleic anhydride utilizing a gaseous flame suppressor mixture with methane, the flow rates in mole percent at critical points in the system were determined. The compositions are expressed in mole percent and based on 100 moles of maleic anhydride produced. The data expressed in Table II represents operation of the system under conditions such that 60 percent and 80 percent, respectively, of the n-butane feed to the oxidation reactor is converted to products. In Table II, the various points are the same as in Table I.

TABLE II

| Component | A | B | C | D | E |
|---|---|---|---|---|---|
| 60 Percent Conversion - Pure Oxygen | | | | | |
| Methane | 10.7 | 9.5 | 17.0 | 22.2 | 3.1 |
| n-Butane | 16.4 | 5.8 | 10.4 | 13.6 | 1.9 |
| Oxygen | 43.9 | 3.0 | 5.3 | 0.9 | 17.2 |
| CO | 1.1 | 8.0 | 14.2 | 2.3 | 45.7 |
| $CO_2$ | 27.9 | 29.8 | 53.0 | 60.9 | 32.0 |
| Maleic Anhydride | — | 5.8 | — | — | — |
| Water | — | 38.1 | — | — | — |
| Total Flow, moles | 1539.3 | 1727.2 | 969.6 | 704.7 | 264.9 |
| 80 Percent Conversion - Pure Oxygen | | | | | |
| Methane | 10.2 | 9.0 | 15.7 | 20.9 | 2.8 |
| n-Butane | 11.9 | 2.1 | 3.7 | 4.9 | 0.6 |
| Oxygen | 43.8 | 3.0 | 5.2 | 0.9 | 16.1 |
| CO | 1.1 | 8.5 | 14.7 | 2.5 | 45.4 |
| $CO_2$ | 32.9 | 35.0 | 60.7 | 70.9 | 35.1 |
| Maleic Anhydride | — | 5.2 | — | — | — |
| Water | — | 37.2 | — | — | — |
| Total Flow, moles | 1714.9 | 1932.9 | 1113.2 | 795.7 | 317.5 |

For the system shown in FIG. 4, maleic anhydride is produced utilizing pure oxygen and a mixture of $CO_2$ and methane as a flame suppressor. The data are presented in Table II.

It will be appreciated that, when carbon dioxide or a substantially unreactive hydrocarbon is the major component of the gaseous flame suppressor in the process of the present invention, it will be necessary initially to add a sufficient amount thereof to the feed to the oxidation reactor to establish the desired concentration thereof, i.e. to prime the system. This is, however, not necessary utilizing oxygen-enriched air as the reactor feed wherein nitrogen is the major component of the gaseous flame suppressor. It will likewise be appreciated that it is within the scope of the present invention to utilize conventional equipment to monitor and automatically regulate the flow of gases within the system so that it can be fully automated to run continuously in an efficient manner.

The process of this invention is advantageous in its simplicity, ease of operation, low capital and operating costs as well as providing a substantially reduced flammability potential. The use of air or oxygen-enriched air as starting material wherein nitrogen is the major component of the gaseous flame suppressor, provides further economic savings. The subject process can be run at a relatively low per pass conversion of the feed hydrocarbon to the desired product to achieve substantially improved selectivity for the subject process. It will be appreciated that a system that achieves enhanced selectivity, and hence increased overall yield of a desired product, is highly advantageous.

We claim:

1. A cyclic process for the production of maleic anhydride comprising:
    (a) reacting a hydrocarbon comprising alkanes and alkenes and an oxygen-containing gas in the vapor phase in the presence of an oxidation catalyst in a reactor vessel under conditions which produce an effluent containing the maleic anhydride at reduced feed conversion and increased product selectivity;
    (b) scrubbing the effluent with a liquid to form a scrubbed liquid phase containing said maleic anhydride and a gaseous phase containing gaseous products including unreacted hydrocarbon;
    (c) recovering said maleic anhydride from the liquid phase;
    (d) introducing the gaseous phase as a pressurized feed into a selective separator to thereby remove a substantial portion of the unreacted reactant hydrocarbon; and
    (e) recycling said substantial unreacted reactant hydrocarbon to said reactor vessel, wherein the process is conducted in the presence of a gaseous flame suppressor, the process being controlled so that flame suppression will be maximized at the point in the process where the pressure is increased, the amount of gaseous flame suppressor being such that the gaseous phase formed in step (b) contains from about 30 to about 95 percent by volume thereof.

2. A process in accordance with claim 1, wherein the alkane is n-butane.

3. A process in accordance with claim 1, wherein the alkene is n-butylene.

4. A process in accordance with claim 1, wherein the oxygen-containing gas is selected from the group consisting of pure oxygen, air and a gas enriched in oxygen relative to air.

5. A process in accordance with claim 4, wherein the oxygen-containing gas is air or a gas enriched in oxygen relative to air and said gaseous flame suppressor comprises a substantially unreactive hydrocarbon containing 1 to 5 carbon atoms, carbon dioxide and nitrogen.

6. A process in accordance with claim 4, wherein the oxygen-containing gas is pure oxygen and said gaseous flame suppressor comprises carbon dioxide and a substantially unreactive hydrocarbon containing 1 to 5 carbon atoms.

7. A process in accordance with claim 1, wherein said selective separator is a pressure swing absorption unit.

8. A process in accordance with claim 7, wherein said pressure swing adsorption unit contains an adsorbent consisting of a silica gel.

9. A process in accordance with claim 7, wherein said pressure swing adsorption unit contains an adsorbent consisting of a zeolite molecular sieve.

10. A process in accordance with claim 7, wherein said pressure swing adsorption unit contains an adsorbent consisting of a zeolite molecular sieve and silica gel.

11. A process in accordance with claim 4, wherein carbon dioxide is a major component of said gaseous flame suppressor and wherein said selective separator is a liquid separator where carbon dioxide is removed from the gaseous phase by dissolution into an absorbent solution.

12. A process in accordance with claim 11, wherein the absorbent solution is an aqueous potassium carbonate solution.

13. A process in accordance with claim 12, wherein at least a portion of the carbon dioxide obtained in said separator is recycled to the effluent formed in step (a), the gas phase formed in step (b) or both of said effluent and said gas phase.

14. A process in accordance with claim 4, wherein carbon dioxide is a major component of said gaseous flame suppressor and wherein said selective separator is a liquid separator where hydrocarbons are removed from the gaseous phase by dissolution in a solvent.

15. A process in accordance with claim 14, wherein the solvent is organic.

16. A process in accordance with claim 6, wherein the gaseous flame suppressor is carbon dioxide and methane, wherein the gas phase formed in step (b) comprises unreacted n-butane, oxygen, carbon dioxide, carbon monoxide and from about 5 to 50 volume percent of methane, and wherein said selective separator is a pressure swing adsorption unit and the removed portion is a gaseous fraction formed therein containing methane and a substantial portion of the unreacted n-butane.

17. A process in accordance with claim 1, wherein the gaseous flame suppressor comprises carbon dioxide, methane and, where said oxygen-containing gas is air of a gas enriched in oxygen relative to air, nitrogen.

18. A process in accordance with claim 1, wherein oxygen is separated from the gaseous phase of step (b) and recycled to said reactor vessel.

19. A cyclic process for the production of phthalic anhydride comprising:
(a) reacting a hydrocarbon comprising xylenes and naphthalenes, and an oxygen-containing gas in the vapor phase in the presence of an oxidation catalyst in a reactor vessel under conditions, which produce an effluent containing the phthalic anhydride and a gaseous phase containing gaseous products including unreacted hydrocarbon;
(c) recovering said phthalic anhydride from the liquid phase;
(d) introducing the gaseous phase as a pressurized feed into a selective separator to thereby remove a substantial portion of the unreacted reactant hydrocarbon; and
(e) recycling said substantial unreacted reactant hydrocarbon to said reactor vessel, wherein the process is conducted in the presence of a gaseous flame suppressor, the process being controlled so that flame suppression will be maximized at the point in the process where the pressure is increased, the amount of gaseous flame suppressor being such that the gaseous phase formed in step (b) contains from about 30 to about 95 percent by volume thereof.

20. A process in accordance with claim 19, wherein the xylene is o-xylene.

* * * * *

UNITED STATES PATENT AND TRADEMARK OFFICE
CERTIFICATE OF CORRECTION

PATENT NO. : 4,987,239

DATED : January 22, 1991

INVENTOR(S) : Ramakrishnan Ramachandran, Yagya Shukla and Donald L. MacLean

It is certified that error appears in the above-identified patent and that said Letters Patent is hereby corrected as shown below:

Column 10, lines 45 & 46: delete "comprising alkanes and alkenes" and insert --selected from the group consisting of alkanes, alkenes and mixtures of these--

Column 10, line 62: delete "substantial"

Column 11, line 23: delete "absorption" and insert --adsorption--

Column 12, line 17: delete "of" and insert --or--

Column 12, lines 24 & 25: delete "comprising xylenes and naphthalenes," and insert --selected from the group consisting of xylenes, naphthalenes and mixtures thereof--

Column 12, lines 29 & 30: delete "and a gaseous phase containing gaseous products including unreacted hydrocarbon;" and insert --at reduced feed conversion and increased product selectivity;--

Column 12, line 31: insert --(b) scrubbing the effluent with a liquid to form a scrubbed liquid phase containing said phthalic anhydride and a gaseous phase containing gaseous products including unreacted hydrocarbon;--

UNITED STATES PATENT AND TRADEMARK OFFICE
CERTIFICATE OF CORRECTION

PATENT NO. : 4,987,239

DATED : January 22, 1991

INVENTOR(S) : Ramakrishnan Ramachandran, Yagya Shukla and Donald L. MacLean

It is certified that error appears in the above-indentified patent and that said Letters Patent is hereby corrected as shown below:

Column 12, line 37, delete "substantial"

Signed and Sealed this

Sixteenth Day of November, 1993

Attest:

BRUCE LEHMAN

*Attesting Officer*     Commissioner of Patents and Trademarks